United States Patent
Schulze

[19]

[11] Patent Number: 5,969,315
[45] Date of Patent: Oct. 19, 1999

[54] DISPLAY DEVICE FOR THE NUMBER OF HEATINGS PERFORMED

[75] Inventor: Dale Schulze, Lebanon, Ohio

[73] Assignee: Ethicon, Inc., Somerville, N.J.

[21] Appl. No.: 08/306,856

[22] Filed: Sep. 15, 1994

Related U.S. Application Data

[63] Continuation of application No. 08/092,734, Jul. 14, 1993, abandoned.

[30] Foreign Application Priority Data

Jul. 31, 1992 [DE] Germany .............................. 42 25 792

[51] Int. Cl.$^6$ .............................. G06M 1/00; G06C 27/00
[52] U.S. Cl. ........................ 235/91 R; 235/103; 235/115; 235/131 R
[58] Field of Search ..................................... 235/103, 115, 235/116, 117 R, 117 A, 118, 122, 91 R, 131 R, 131 FD, 131 M, 131 JA

[56] References Cited

U.S. PATENT DOCUMENTS

| | | | |
|---|---|---|---|
| 2,476,560 | 7/1949 | Norgard | 235/117 R |
| 2,762,567 | 9/1956 | Van Veen | 235/117 R |
| 3,178,109 | 4/1965 | Farrell et al. | 235/91 |
| 3,428,324 | 2/1969 | Weisbecker | 235/122 |
| 3,713,582 | 1/1973 | Furuoka | 235/116 |
| 3,720,898 | 3/1973 | Levinn | 337/95 |
| 4,235,842 | 11/1980 | Thomas et al. | 422/116 |
| 5,090,033 | 2/1992 | Murray-Shelley | 377/28 |
| 5,300,087 | 4/1994 | Knoepfler | 606/207 |
| 5,304,190 | 4/1994 | Reckelhoff | 606/170 |

FOREIGN PATENT DOCUMENTS 207224  2/1940  Germany .

*Primary Examiner*—Eddie C. Lee
*Attorney, Agent, or Firm*—Paul A. Coletti

[57] ABSTRACT

A display device is described which indicates the number of heatings performed, especially for the purpose of autoclave sterilization. The display device comprises a temperature-sensitive mechanical element which essentially reversibly transforms from a first spatial state to a second spatial state when the temperature-sensitive mechanical element is heated in excess of a predetermined temperature. The temperature-sensitive mechanical element is coupled to the actuating element of a counter mechanism and upon the transformation to the second spatial state effects movement of the actuating element into an actuation position.

5 Claims, 6 Drawing Sheets

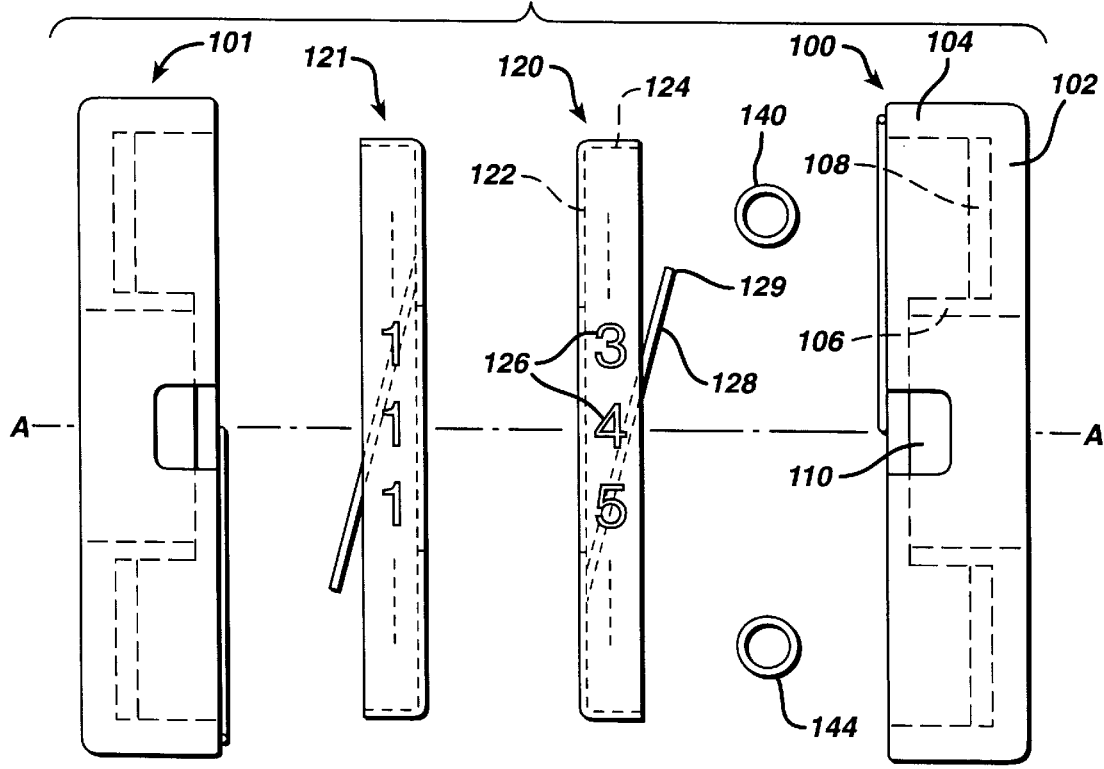
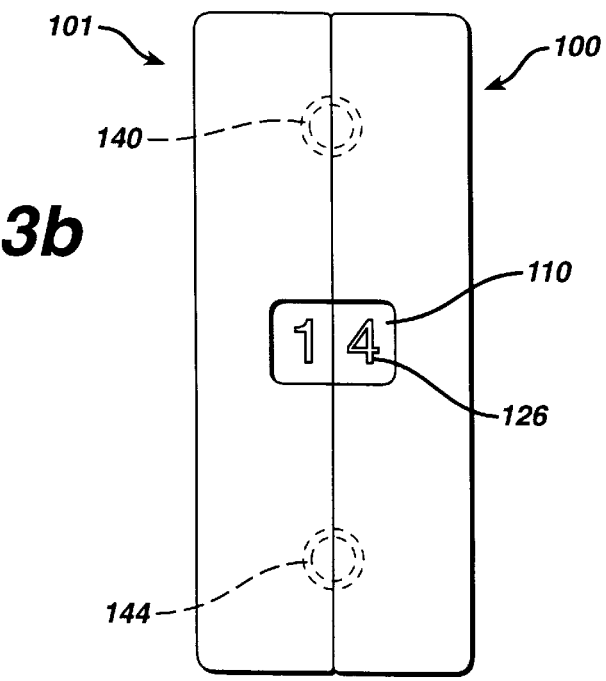

DISPLAY DEVICE FOR THE NUMBER OF HEATINGS PERFORMED

This is a continuation, of application Ser. No. 08/092,734, filed Jul. 14, 1993 now abandoned.

PRIORITY DATA

This application claims priority from DE P 42 25 792.1, filed Jul. 31, 1993, entitled "Display Device for the Number of Heating Performed."

FIELD OF THE INVENTION

The present invention is directed to a display device for a surgical instrument, to disclose the number of heatings performed on the instrument, particularly useful for the purpose of autoclave sterilization.

BACKGROUND OF THE INVENTION

Conventionally, surgical instruments have been made of metal. In this case there is no problem in sterilizing the instruments using an autoclave where they are heated up 135° C. The application of plastics for surgical instruments, however, has some advantages over metal: it can easily be molded in complicated shapes, it has a light weight, and it is less expensive than metal. Especially for elaborate instruments, such as those used in minimally invasive surgery or in laparoscopic operations, there is a trend to manufacture from plastics.

In many cases, the whole instrument or part of the instrument is designed to be disposable after the operation. To save costs it is often advantageous if the instrument has some reusable parts, which have to sterilized in an autoclave after the operation. Some plastic materials can resist heightened temperatures during this process (120° C. to 135° C.), for instance, polyetherimide. Generally, even these plastic instruments by autoclave only for a limited number of times (on the order of 10 times), because they age, crack, etc. Consequently the instruments are less reliable after having been heated too often.

SUMMARY OF THE INVENTION

It is an object of the present invention to provide a means for indicating the number of heatings on a surgical instrument, which is reliable, inexpensive and small.

This problem is solved through the use of a display device for the number of heatings performed, particularly for the purpose of autoclave sterilization, having the features of the device described herein. The display device according to the invention can be manufactured in small size, so that it can be easily attached to a "semi"-disposable surgical instrument for indicating the number of times the instrument has been subjected to high heat. It is also possible to equip a reusable instrument with the display device according to the invention, e.g. to indicate the need for maintenance.

In the display device according to the present invention, a temperature-sensitive mechanical element (such as a bi-metallic strip) changes its size when it is heated to high temperature. This element is coupled to an actuating element of a counter, thus increasing the number of symbol displayed on the counter each time the temperature-sensitive mechanical element actuates the actuating element. The number or other symbol displayed by the counter is easily visible, so that the person using a surgical instrument having the display device according to the invention is thereby informed of the number of times the instrument has been heated (and thus of the instrument's residual lifetime).

Preferably the temperature-sensitive mechanical element is made of a memory metal, for example of a nickel titanium alloy. Such a memory metal element can be made to expand or contract at a predetermined temperature. A memory metal has faster response time than bimetallics, and the alloy can be custom-designed to actuate the temperature-sensitive member at a desired temperature. For example, the temperature-sensitive mechanical element can be made in the form of a memory spring that expands a great deal when heated and which essentially reversibly returns to its original shape after cooling to the original temperature. Preferably, in its original shape (or first spatial state) the memory metal spring is somewhat biased by a reset spring in order to re-define the original shape precisely. When the memory metal spring is heated above the predetermined temperature and it expands to its second spatial state, it is strong enough to overcome the reset spring.

Preferably the counter on the present display device comprises a ratcheting device.

In an advantageous embodiment after a predetermined number of actuations of the counter has been exceeded a first blocking element coupled to the counter moves to a blocking position. In this, the blocking element may inhibit use of the whole surgical instrument, e.g., by blocking an inhibit use of the whole surgical instrument, e.g. by blocking an actuation knob. Similarly, a second blocking element may be coupled to the temperature-sensitive mechanical element, or to a second temperature-mechanical element being responsive to a higher temperature than the ordinary temperature experienced during autoclave sterilization. This second blocking element inhibits the surgical instrument completely and irreversibly when the instrument has been heated to too high a temperature and, in doing so, has potentially been made unreliable.

DESCRIPTION OF THE DRAWINGS

In the following the present invention is described in more detain by reference to some embodiments. The drawings show:

FIG. 3a an exploded side view of a third embodiment of the present invention, showing some parts in section;

FIG. 3b a side view of the third embodiment;

DESCRIPTION OF THE INVENTION

Figure 1:
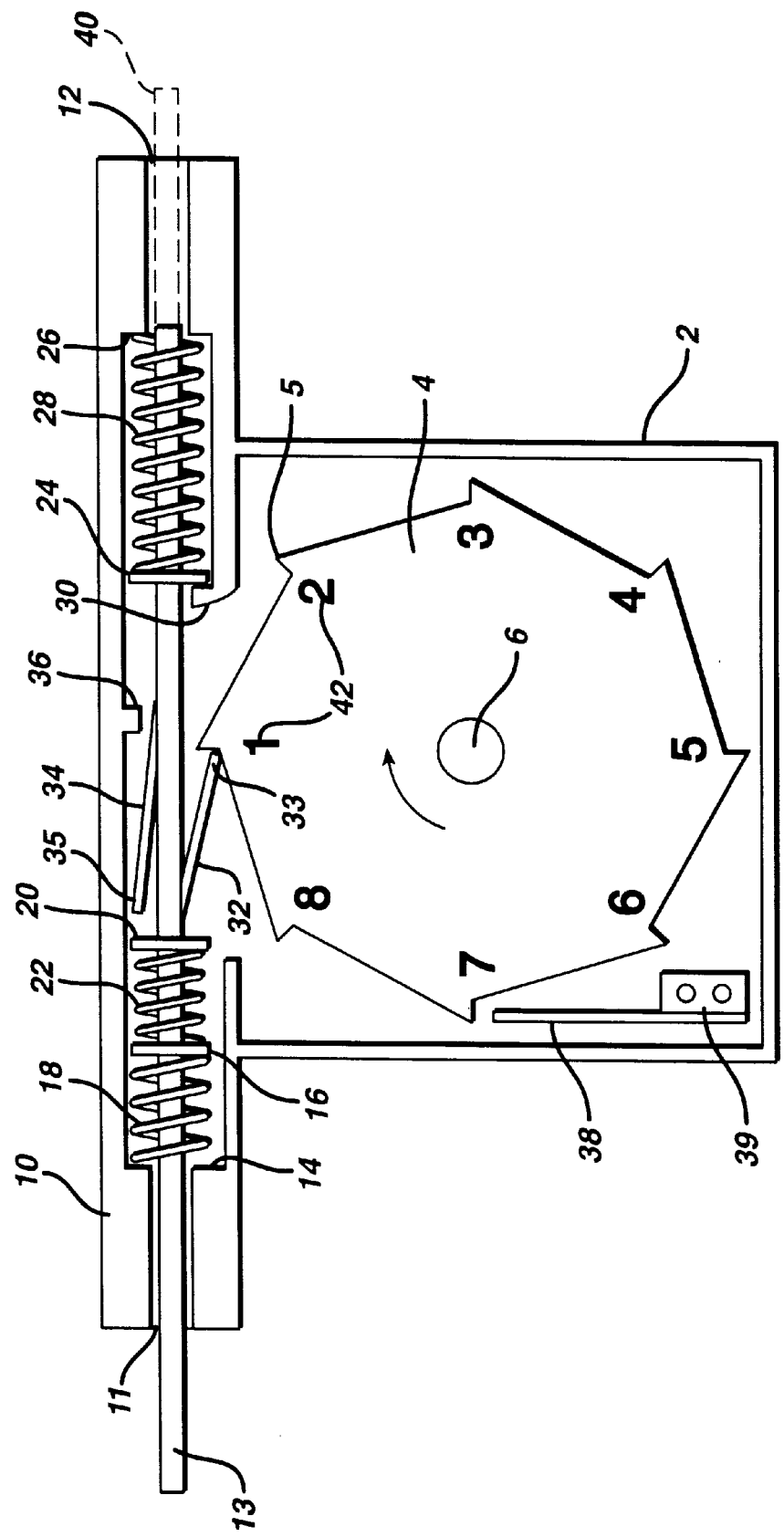
FIG. 1 a sectional view of a first embodiment of the present invention.

FIG. 1 illustrates a first embodiment according to the present invention. In housing 2, ratchet wheel 4 (having teeth 5) is rotatably mounted by means of a pivot 6. In an upper portion 10 of the housing 2, a shaft 13 is slidably supported in guide holes 11, 12. A safety spring 18 is located between an abutting surface 14 and a first disk 16 which is, in turn, slidably mounted on the shaft 13. A spring 22 serves as temperature-sensitive mechanical element and is mad of a suitable memory metal alloy. Spring 22 abuts against the first disk 16 and a second disk 20 which is rigidly attached to the shaft 13. A reset spring 28 made of ordinary metal is held between a third disk 24 which is rigidly attached to the shaft 13, and an abutting surface 26. In the resting position of the device in which the temperature-sensitive mechanical element (spring 22) is in first spatial state, the rest spring presses the third disk 24 against a protrusion 30, as shown in FIG. 1. In this state spring 22 is slightly compressed.

One end of a ratchet 32 in the form of a leaf spring is fixed to the bottom side of shaft 13. The ratchet 32 is biased against the ratchet wheel 4, so that its free end 33 touches the ratchet wheel 4 along its periphery, i.e., along the sides of the teeth 5. A safety ratchet 34 in form of a leaf spring is fixed at the upper side of shaft 13 close to the third disk 24. The free end 35 of safety ratchet 34 can be depressed by means of a protrusion 36 of upper portion 10. In the lower part of the housing 2 a second ratchet 38 is attached by means of a support member 39.

On the ratchet wheel 4 there are provided display numbers 42, each display number 42 being associated to an individual tooth 5. A cover plate of housing 2 comprises a window (not shown in FIG. 1) through which one of the display numbers 42 is visible. Preferably the display numbers 42 are arranged in consecutive order; it is also possible to use some other kind of display signs or symbols, e.g. a color code an the like.

The following describes how the display device according to the first embodiment of the present invention works. FIG. 1 displays the resting position of the device in which spring 22 is its first spatial state, i.e. a compressed state. It is noted that it is not necessary to bias spring 22 to a compressed configuration, because it is made of a memory metal and will expand greatly in this embodiment upon heating and almost reversibly return to its original size upon cooling. Some compression of spring 22 in its resting position is advantageous, however, because in this way the resting position of the ratchet 32, which serves as the actuating element of the counter, is well defined by means of the reset spring 28, the third disk 24 and the protrusion 30.

When the display device and the surgical instrument to which it is attached are heated, e.g. in an autoclave, spring 22 expands whereas safety spring 18 keeps its original size as long as the device is not heated to too high a temperature. The expanding spring 22 moves the shaft 13 to the right side of FIG. 1 so that spring 22 causes compress in of the reset spring 28. During the movement of the shaft 13, the free end 33 of ratchet 32 engages a tooth 5 closest to it and rotates the ratchet wheel 4 in a clockwise sense. When the ratchet 32 has reached its actuating position (spring 22 is in its second spatial state now), the ratchet wheel 4 has been rotated by one tooth, i.e. until the second ratchet 38 snaps across the tip of the tooth it is biased against.

When the temperature decreases, the spring 22 returns to its first spatial state, i.e., the resting position shown in FIG. 1. The friction between the free end 33 and the ratchet wheel 4 does not cause the ratchet wheel 4 to rotate counterclockwise again, because such rotation is inhibited now by second ratchet 38.

This embodiment further comprises the safety spring 18 by means of which it is possible to lock the whole surgical instrument to which the display device is attached to, in case the instrument is exposed to a dangerously high temperature which would render it inoperative for future use. If the temperature exceeds a predetermined level (being higher than the response temperature of spring 22) the safety spring 18 (as well as spring 22) expands, so that the total displacement of shaft 13 is large enough for the free end 35 of safety ratchet 34 to engage the right side of protrusion 30 as in FIG. 1. When that happens shaft 13 cannot retract to its original position after cooling. Furthermore, the end 40 of shaft 13 will project from the upper portion 10 of the housing 2 as shown in dotted lines in FIG. 1. The end 40 can serve as a blocking element by locking, e.g., ac actuating knob of the surgical instrument.

Figure 2A:
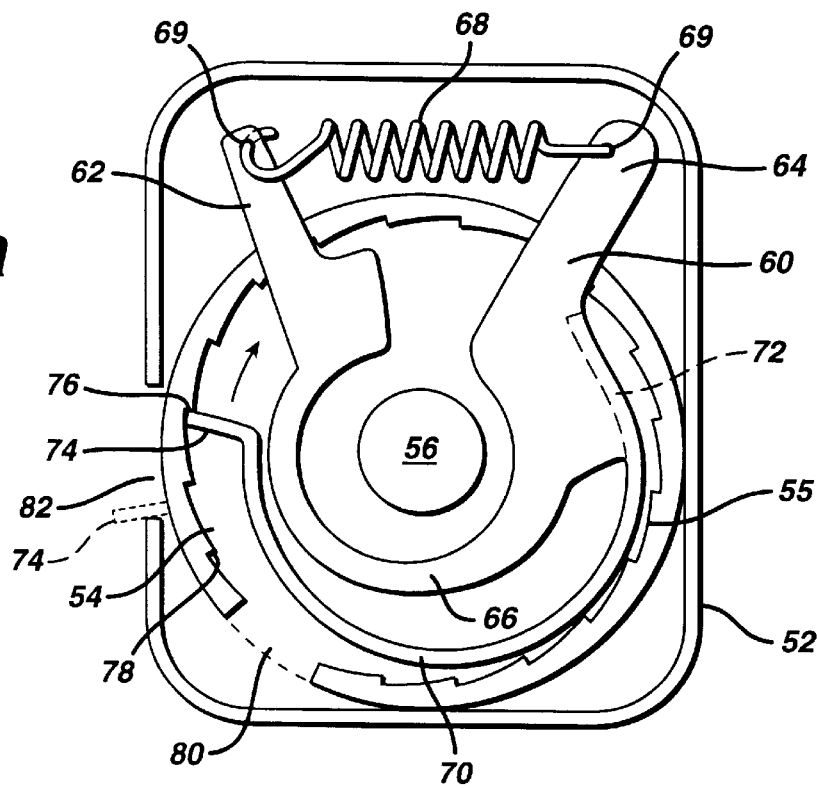
FIG. 2a a top of a second embodiment of the present invention, having a top plate of the housing removed.
Figure 2B:
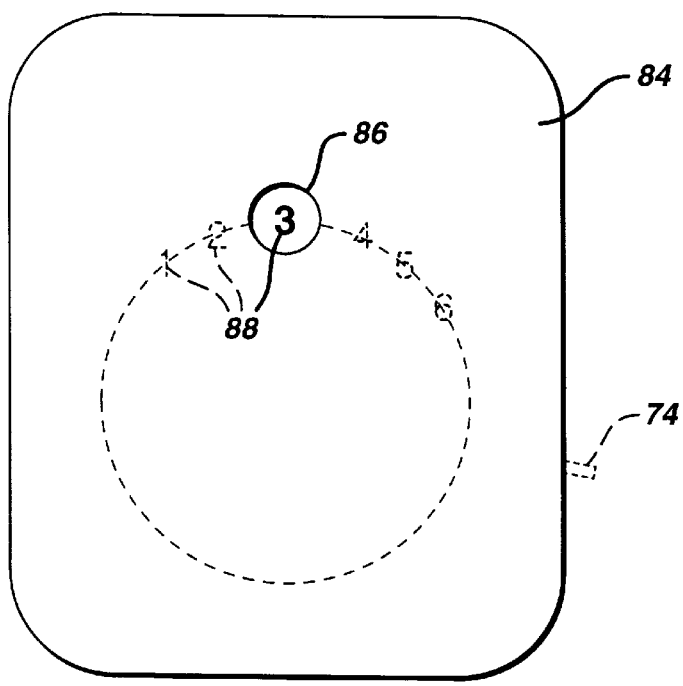
FIG. 2b a bottom view of the second embodiment

FIGS. 2a and 2b show a second embodiment of the present invention. In a housing 52 a ratchet wheel 54 is rotatably mounted by means of a pivot 56. The ratchet wheel 54 has the general shape of an open cylinder having a toothed ring 55 its interior area. A spring member 60 comprising a first leg 62, a second leg 64 and a resilient arcuate portion 66 portion 66 is biased in such a way as to increase the distance between the first leg 62 and the second member 60 is rigidly fixed to housing 52. A spring 68 made of a memory metal alloy is attached to the spring member 60 by inserting the ends of the spring 68 through holes 69 in the first leg 62 and the second leg 64. Along the side of the second leg 64 the fixed end 72 of a ratchet spring 70 is rigidly attached to the second leg 64. The ratchet spring 70 is a form of arcuate leaf spring with its longer side extending along approximately half of the inner periphery of ratchet wheel 54, whereas its smaller side extends perpendicularly to the plane of FIG. 2a. The free end 74 of ratchet spring 70 is bend outwardly against teeth 76.

In order to enable to a safety function which will be described later the toothed ring 55 comprises a gap 80 and the housing 52 includes a side window 82.

FIG. 2b shows the display device of FIG. 2a from the other side, i.e. the bottom side of ratchet wheel 54. (Instead of display numbers it is possible to use other kinds of symbols.)

This embodiment of the inventive display device works in the following way. In its first spatial state, i.e. at low temperature, the spring 68 has a short length, and it is strong enough to bias the arcuate portion 66 of spring member 60. In this state (which is not shown in FIG. 2a) the second leg 64 is moved to the left and consequently the free end 74 of the ratchet spring 70 is moved downwardly.

Now, when the temperature is raised above the predetermined temperature the spring 68 expands and allows the spring member 60 to relax. Consequently, the second leg 64 moves to the right and the free end 74 of the ratchet spring 70 moves upwardly to the position seen in FIG. 2a. Because it engages the steep-sloped side of a tooth 76 of the ratchet wheel 54 it rotates the ratchet wheel 54 in a clockwise sense by one tooth width, exhibiting the next display number 88. As the temperature decreases the spring contracts, biases the spring member 60 and moves the free end 74 of the ratchet spring 70 downwardly until it snaps across the tip of the subsequent tooth.

The safety feature provided by this embodiment is able to block the surgical instrument the device is attached to after a predetermined number of sterilizations has been performed. After the last allowed heating process the free end 74 of the ratchet spring 70 engages at the edge 78. When the device is sterilized another time, on cooling the free end 74 reaches the upper end of gap 80. Because the ratchet spring 70 is biased outwardly, spring 70 is no longer supported by the toothed ring 55 and thereby penetrates the side window 82, as shown in FIG. 2a and FIG. 2b in dotted lines. In a similar manner as the blocking device according to the first embodiment, the protruding free end 74 is able to lock the whole surgical instrument in order to inhibit its future use.

Figure 3C:
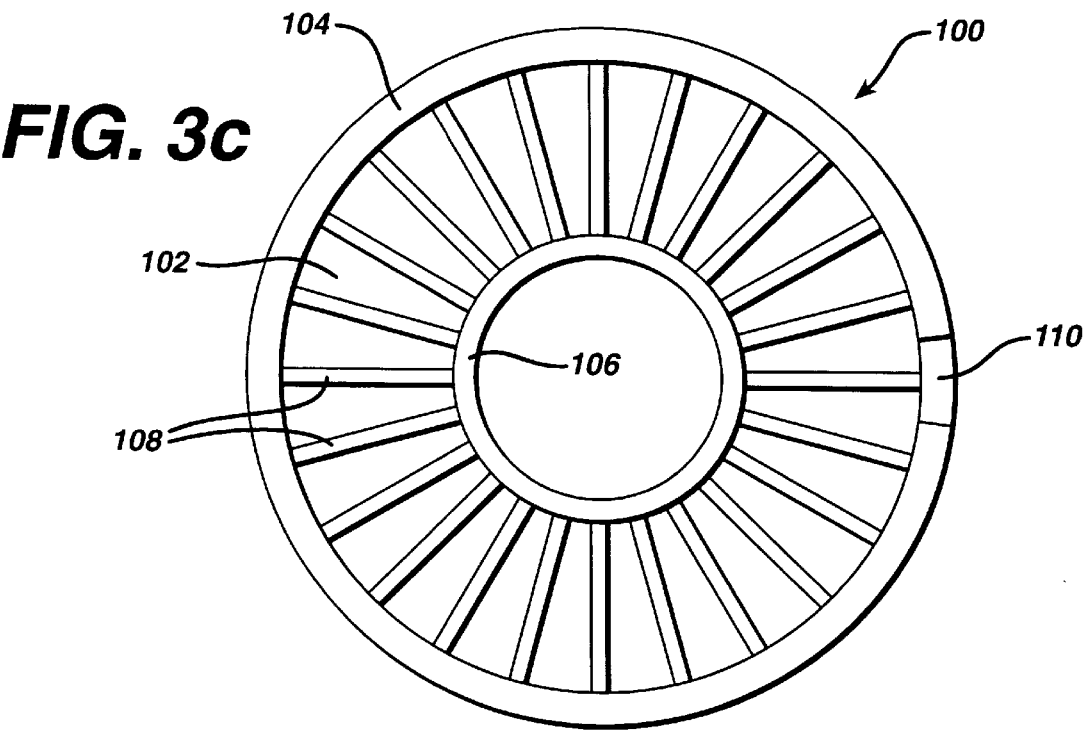
FIG. 3c a top view of the inside of one of the halves of the housing of the third embodiment.

A third embodiment of the present invention is illustrated in FIGS. 3a–3f. FIG. 3a shows the individual members of this embodiment in exploded side view. A first half-shell 100 of the housing of the display device, a second half-shell 101 of the housing, a first counting wheel 120, and a second counting wheel 121 are concentrically aligned along an axis A—A which is the rotation axis of the counting wheels 120, 121.

The first half-shell 100 of the housing comprises a bottom portion 102, a lateral area 104 forming the outer periphery, and a generally cylindrical bearing member 106 whose axial extension is somewhat smaller than that of the lateral area 104 (see FIG. 3a). Radially extending ribs 108 are formed on the inner surface of the bottom portion 102, as shown in FIG. 3c. A window 110 is located in the lateral area 104. The construction of the second half-shell 101 of the housing is the same as that of the first half-shell 100. Preferably both half-shells 100, 101 are molded from a suitable temperature-resistant plastic or other temperature resistant material.

A first counting wheel 120 generally has the shape of an open cylinder. A hub portion 122 is supported by the bearing member 106 of the first half-shell 100 of the housing, and a lateral area 124 is adapted to fit into the first half-shell 100 of the housing. Display numbers 126 or similar display signs are arranged on the outer lateral area 124, see FIG. 3a. On the hub portion 122 is formed an arcuate ratchet 128 which is bend toward the facing bottom portion 102, so that the free end 129 of the ratchet 128 resiliently abuts against the bottom portion 102 including the ribs 108 (See also FIG. 3d.) In the center of the first counting wheel 120 is provided a center hole 132 the diameter of which corresponds to that of the bearing member 106. A generally tangentially extending arcuate first opening 134 having a nose 135 is formed close to the periphery of the hub portion 122. A similar second opening 136 having a nose 137 is provided approximately diametrically opposite to the first opening 134.

Figure 3D:
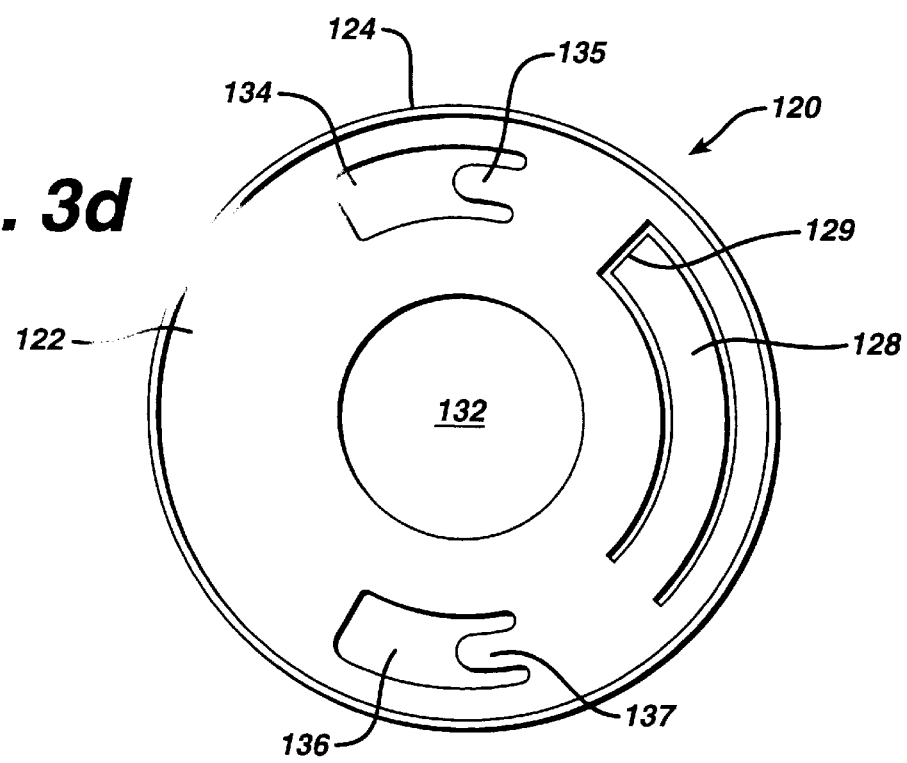
FIG. 3d a top view of one of the counting wheels of the third embodiment.

If the first counting wheel 120 is inserted in the first half-shell 100 of the housing, the ratchet 128 enables rotation of the first counting wheel 120 in one direction only, which is the clockwise sense in FIG. 3d. A counterclockwise rotational movement is inhibited, because in this case the free end 129 of the ratchet 128 engages an edge between the bottom portion 102 and rib 108 and cannot come across the rib 108. The second counting wheel 121 is inserted into the second half-shell 101 of the housing, so that the hub portions of the counting wheels 120, 121 face each other (see FIG. 3a) counting wheel 121 is constructed in essentially the same way as the first counting wheel 120, except that its ratchet is arranged in away that both counting wheels 120, 121 can be rotated in the same direction only.

Preferably the counting wheels 120, 121 are made of stainless steel.

The second counting wheel 121 is arranged with respect to the first counting wheel 120, so that the first opening 134 of the first counting wheel 120 roughly coincides with a corresponding first opening in the hub portion of the second counting wheel 121. The same holds for the second opening 136 of the first counting wheel 120 and a corresponding one in the second counting wheel 121. A helical spring 140 made of a memory metal alloy is inserted into the first opening 134 of the first counting wheel 120 where its first end 142 (see FIG. 3e) is held by the nose 135. The second end 143 of the helical spring 140 is similarly held by a corresponding nose in the first opening of the second counting 121. In this way the helical spring 140 exerts a force onto the first counting wheel 120 via its first end 142 and a force onto the second counting wheel 121 via its second end 143. Another helical compression spring 144 made of an ordinary material is inserted into the second opening 136 of the first counting wheel 120 and into a corresponding second opening of the second counting wheel 121. This helical spring 144 presses against the first counting wheel 120 via its first end 146 where spring 144 is held by the nose 137, and spring 144 presses against the second counting wheel 121 via its second end 147 where a similar nose is provided. The position of the helical springs 140 and 144 with respect of the planes of the hub portions of the counting wheels 120 and 121 is illustrated in FIG. 3b.

Figure 3E:
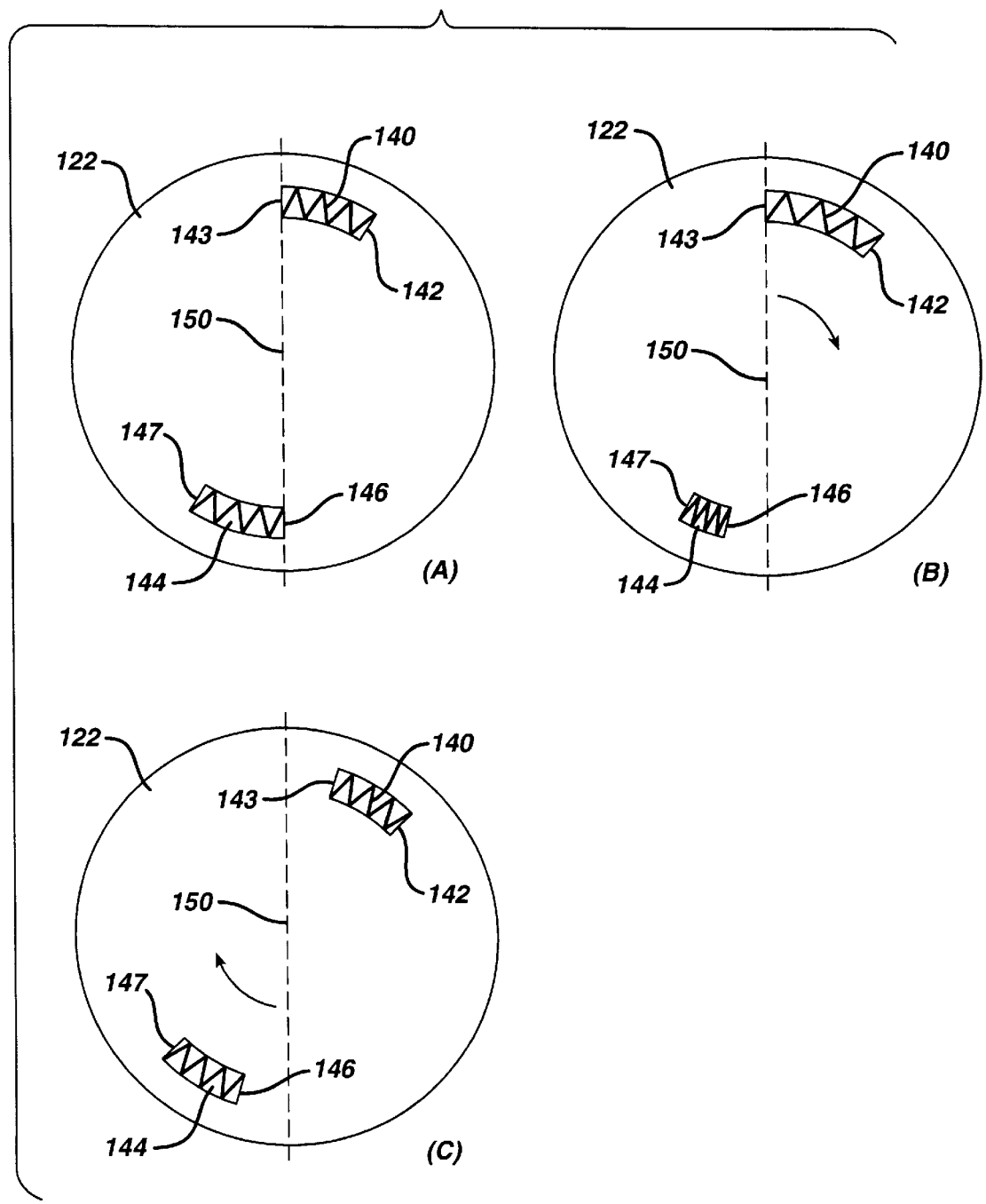
FIG. 3e a diagrammatic view illustrating the function of the display device according to the third embodiment.

The display device according of the third embodiment of this invention works is explained using FIG. 3e. Part (A) of FIG. 3e shows the resting position of the device in which the helical memory metal spring 140 which is the temperature-sensitive mechanical element, is in its first spatial state and in which the first counting wheel 120 serving as the actuating element of the counter is in its resting position. When the display device is heated, the helical spring 140 of memory metal expands while it is able to exert a higher force than the ordinary helical spring 144. The helical spring 140 tries to rotate the first counting wheel 120 in a clockwise sense via its first end 142 and to rotate the second counting wheel 121 in a counterclockwise sense via its second end 143. The latter is not possible, because the free end of the ratchet of the second counting wheel 121 abuts against an edge between the bottom portion and a rib of the second half-shell 101 of the housing. As a result of the clockwise rotation by an amount corresponding to the width (better said, angle) between two adjacent ribs, the next display number 126 is moved to the window 110 to indicate the completion of a single process. Furthermore, the helical spring 144 is compressed, see part (B) of FIG. 3e where the line 150 serves as an aid the eye. Now the helical spring 140 of memory metal is in its second spatial state and the first counting wheel 120 is in its actuating position.

In the last step of the counting process which is illustrated in part (C) of FIG. 3e the display device cools, the helical spring 140 of memory metal contracts and the helical spring 144 of ordinary material is able to exert a larger force than the memory metal spring. This means that the helical spring 144 tries to rotate the first counting wheel 120 in a counterclockwise sense and to rotate the second counting wheel 121 in a clockwise sense. The former is not possible, because in this direction the ratchet 128 of the first counting wheel 120 blocks. As a result, the second counting wheel 121 is rotated by an amount corresponding to the width between two adjacent ribs in the bottom portion of the second half-shell 101 of the housing.

In the embodiment the second half-shell 101 comprises a window, display numbers or symbols, preferably the first digit of a display number, can be provided on the lateral are of the second counting wheel 121, as shown in FIGS. 3a and 3b. It is noted, however, that during each actuation of the display device both counting wheels 120, 121 are rotated by the same angle. Consequently the counting wheels 120, 121 do not form a counter having a decimal numbers or symbols associated to one of the counting wheels 120 or 121 is sufficient.

Figure 3F:
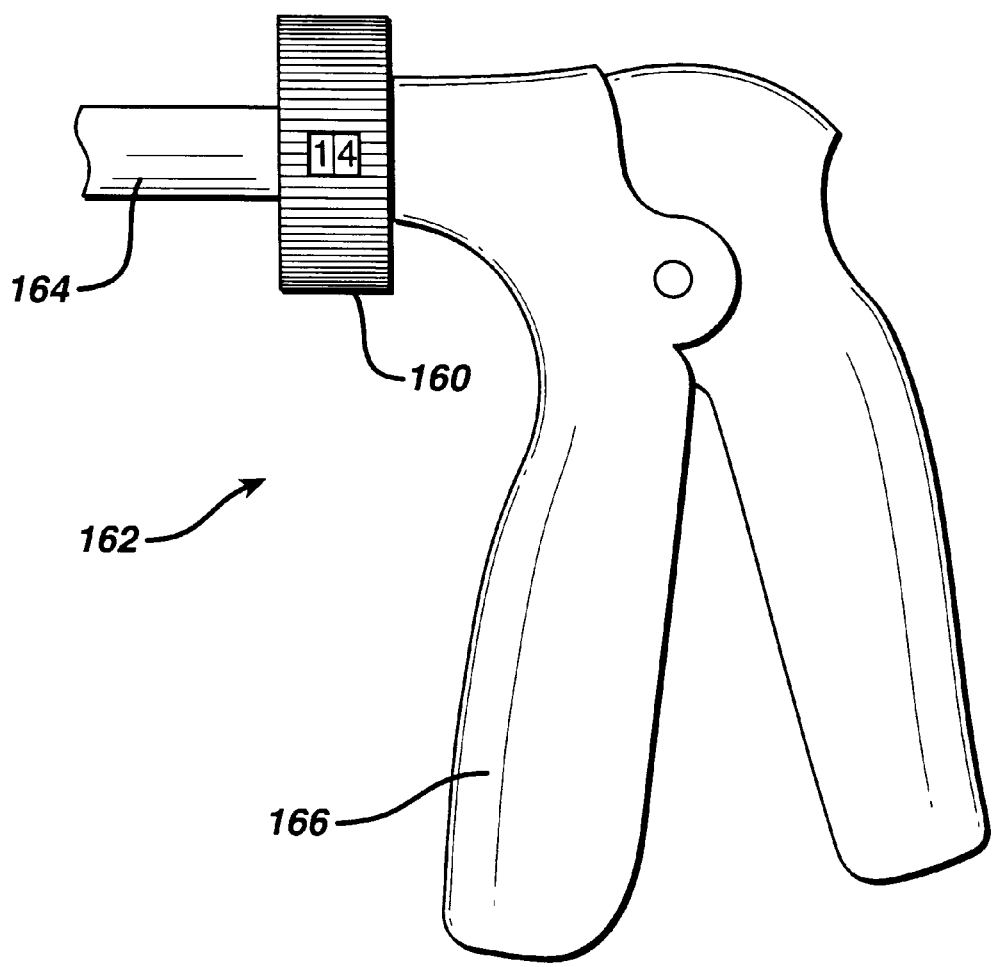
FIG. 3f a side view of the display device according to the third embodiment attached to a surgical instrument.

FIG. 3f illustrates how the display device according to the third embodiment of the invention can be attached to a surgical instrument. In this example the surgical instrument 162 is applied in laparoscopy and comprises a handle member 166, an instrument tube 164 and at the distal end (not shown) an operational tool like a needle holder or a clamp, etc. To reduce costs, some parts of the instrument are semi-reusable, e.g. the instrument tube 164 and the handle member 166. For monitoring the number of times these parts have been exposed to high temperatures during sterilization, a display device 160 is attached to the instrument tube 164, the inner diameter of the bearing member 106 and the diameter of the center hole 132 fitting to the outer diameter of the instrument tube 164.

There are various ways to attached a counter device according to the invention to a surgical instrument. Another example is to include it in the handle member of the surgical instrument. In any event, this device can perform both the counting and blocking function by meeting with the recycled moving shaft of a surgical instrument, as described above.

I claim:

1. A device for monitoring the number of times a sterilization has been performed comprising:

a temperature sensitive mechanical element which transforms from a first spatial state to a second spatial state at a predetermined temperature; and a blocking element coupled to said mechanical element movable from a retracted position to an extended blocking position when the number of heatings of said temperature sensitive mechanical element beyond a predetermined temperature exceed a predetermined number of such heatings; and said monitoring device capable of blocking operation of a surgical instrument when said blocking element is in said extended position.

2. A device according to claim 1, characterized in that said temperature-sensitive mechanical element is made of a memory metal.

3. A device according to claim 2, characterized in that said memory metal is a nickel titanium alloy.

4. A device according to claim 1, characterized in that said temperature-sensitive mechanical element is made of a bimetal.

5. A device for monitoring the number of times a sterilization has been performed comprising:

a temperature sensitive mechanical element which transforms from a first spatial state to a second spatial state at a predetermined temperature; and a blocking element coupled to said mechanical element movable from a retracted position to an extended blocking position when the number of heatings of said temperature sensitive mechanical element beyond a predetermined temperature exceed a predetermined number of such heatings; and said monitoring device capable of blocking operation of a surgical instrument when said blocking element is in said extended position; and a display device attached to said temperature sensitive element in order to indicate the number of times said element has transferred from said first state to said second state.

* * * * *